United States Patent
Pavlidis

(10) Patent No.: US 6,996,256 B2
(45) Date of Patent: Feb. 7, 2006

(54) DETECTION SYSTEM AND METHOD USING THERMAL IMAGE ANALYSIS

(75) Inventor: Ioannis Pavlidis, Minneapolis, MN (US)

(73) Assignee: Honeywell International Inc., Morristown, NJ (US)

( * ) Notice: Subject to any disclaimer, the term of this patent is extended or adjusted under 35 U.S.C. 154(b) by 609 days.

(21) Appl. No.: 09/776,470

(22) Filed: Feb. 2, 2001

(65) Prior Publication Data

US 2005/0259849 A1    Nov. 24, 2005

Related U.S. Application Data

(60) Provisional application No. 60/210,279, filed on Jun. 8, 2000.

(51) Int. Cl.
G06K 9/00    (2006.01)

(52) U.S. Cl. .................. 382/118; 382/128

(58) Field of Classification Search ............ 382/115, 382/117, 118, 128; 340/575, 5.53, 5.83
See application file for complete search history.

(56) References Cited

U.S. PATENT DOCUMENTS

| | | |
|---|---|---|
| 2,944,542 A | 7/1960 | Barnett et al. |
| 3,847,142 A | 11/1974 | Williams, Jr. et al. |
| 4,403,615 A | 9/1983 | Hoehner |
| 4,500,784 A | 2/1985 | Hacskaylo |
| 4,520,504 A | 5/1985 | Walker et al. |
| 4,878,116 A | 10/1989 | Thomas et al. |
| 4,940,059 A | 7/1990 | Voelz |
| 5,013,917 A | 5/1991 | Ulich |
| 5,099,852 A | 3/1992 | Meister et al. |
| 5,221,919 A | 6/1993 | Hermans |
| 5,287,183 A | 2/1994 | Thomas et al. |
| 5,339,817 A | 8/1994 | Nilsson |
| 5,361,769 A | 11/1994 | Nilsson |
| 5,363,311 A | 11/1994 | Garbo |
| 5,370,121 A | 12/1994 | Reichenberger et al. |
| 5,406,956 A | 4/1995 | Farwell |
| 5,507,291 A | 4/1996 | Stirbl et al. |
| 5,603,328 A | 2/1997 | Zucker et al. |
| 5,689,241 A * | 11/1997 | Clarke et al. ............... 340/575 |
| 5,703,367 A | 12/1997 | Hashimoto et al. |
| 5,771,261 A | 6/1998 | Anbar |
| 5,774,571 A | 6/1998 | Marshall |
| 5,860,922 A | 1/1999 | Gordon et al. |
| 5,860,935 A | 1/1999 | Blaszynski et al. |
| 5,876,334 A | 3/1999 | Levy |
| 5,900,942 A | 5/1999 | Spiering |
| 5,940,139 A | 8/1999 | Smoot |

(Continued)

FOREIGN PATENT DOCUMENTS

EP    0867830 A    9/1998

(Continued)

OTHER PUBLICATIONS

Fendt et al., "The neuroanatomical and neurochemical basis of conditioned fear," *Neurosci Biobehav Rev*, 23(5):743-60 (May, 1999).

(Continued)

*Primary Examiner*—Vikkram Bali
(74) *Attorney, Agent, or Firm*—Kris F. Fredrick

(57) ABSTRACT

Thermal image data of at least a region of a face of a person is provided. The thermal image data is used to determine a physiological state of a person, e.g., anxiety. For example, anxiety may be determined by a comparison of the thermal image data to a baseline, or by comparison of thermal image data for one region of the person's face to another.

18 Claims, 7 Drawing Sheets

U.S. PATENT DOCUMENTS

| | | | |
|---|---|---|---|
| 6,002,505 | A | 12/1999 | Kraenert et al. |
| 6,464,646 | B1 | 10/2002 | Shalom et al. |
| 6,757,412 | B1 | 6/2004 | Parsons et al. |
| 2002/0062089 | A1 | 5/2002 | Johnson, Jr. |
| 2002/0091336 | A1 | 7/2002 | Cohen |
| 2002/0183627 | A1 | 12/2002 | Nishii et al. |
| 2003/0012253 | A1 | 1/2003 | Pavlidis |
| 2003/0016726 | A1 | 1/2003 | Pavlidis |
| 2003/0120140 | A1 | 6/2003 | Bango |
| 2003/0204144 | A1 | 10/2003 | Lin |

FOREIGN PATENT DOCUMENTS

| | | |
|---|---|---|
| EP | 0 885 587 A1 | 12/1998 |
| JP | 59195134 A | 11/1984 |
| WO | 9216910 A | 10/1992 |
| WO | 98/08431 | 3/1998 |
| WO | 9906974 A | 2/1999 |

OTHER PUBLICATIONS

Jacquez et al., "The spectral reflectance of human skin in the region 0.7-2.6 μm," *Technical Report, 189*, Army Medical Research Laboratory, Fort Knox (Apr., 1955).

Jordan et al., "Hierarchical Mixtures of Experts and the EM Algorithm," *Neural Computation, 6*, pp. 181-214 (1994).

Levin et al., "The energy expended in chewing gum," *New England Journal of Medicine, 341*(27):2100 (Dec., 1999).

Mendez, *The Master of Disguise*, William Morrow and Co., New York, N.Y.; cover page, title page, copyright page and table of contents only; 4 pgs. (1999).

Moghaddam et al., "Probabilistic Visual Learning for Object Recognition," *IEEE Trans. Pattern Analysis and Machine Intelligence, 19*(7):696-710 (Jul., 1997).

Otsu, "A Threshold Selection Method from Gray-Level Histograms," *IEEE Trans. Systems, Man And Cybernetics,* 9:(1)62-65 (Jan., 1979).

Pavlidis et al., "Automatic passenger counting in the high occupancy vehicle (HOV) lanes" *Proceedings 1999 Annual Meeting of the Intelligent Transportation Society of America*, Washington, D.C. (Apr. 19-22, 1999).

Pavlidis et al., "A near-infrared fusion scheme for automatic detection of vehicle passengers," *Proceedings 1999 IEEE Workshop on Computer Vision Beyond the Visible Spectrum: Methods and Applications*, 41-48, Fort Collins, C.O. (Jun. 22, 1999).

Penev et al., "Local feature analysis: a general statistical theory for object representation," *Network: Computation in Neural Systems, 7*(3):477-500 (Aug., 1996).

Pentland et al., "Face recognition for smart environments," *IEEE Computer, 33*(2):50-55 (Feb., 2000).

Phillips et al., "The FERET database and evaluation procedure for face-recognition algorithms," *Image and Vision Computing, 16*(5):295-306 (Apr., 1998).

Prokoski "Disguise detection and identification using infrared imagery," *Proceedings of SPIE, Optics, and Images in Law Enforcement II, 339*:27-31, A.S. Hecht, ed., Arlington, V.A. (May, 1982).

Sabins, *Remote Sensing, Principles and Interpretation*, W.H. Freeman and Company, New York, N.Y.; cover page, title page, copyright page and table of contents only; 7 pgs. (1997, 3rd ed.).

Sliney, "Laser and LED eye hazards: safety standards," *Optics and Photonics News*, pp 32- (Sep., 1997).

Visionics Corporation, "Face detection constantly searches for faces in a datastream" Jersey City, N.J.; retrieved from the Internet on Jun. 25, 2001, <URL:http://www.visionics.com/faceit/tech/detect.html>, 1 pg.

Wiskott et al., "Face recognition by elastic bunch graph matching," *IEEE Trans. Pattern Analysis and Machine Intelligence, 19*(7):775-779 (Jul. 1997).

Zhu et al., "Region Competition: Unifying Snakes, Region Growing, and Bayes/MDL for Multiband Image Sementation," IEEE Transactions on Image Analysis and Machine Intelligence, 18(9) (Sep., 1996). 884-900.

Fujimasa et al., "Converting Far-Infrared Image Information to Other Physiological Data," *IEEE Engineering in Medicine and Biology*, vol. 19, No. 3, pp. 71-75, 2000.

Gose et al., "Pattern Recognition and Image Analysis," pp. 159-186, Prentice Hall, Upper Saddle River, New Jersey (1996).

Holden, "Panel Seeks Truth in Lie Detector Debate," Science, vol. 291, No. 9, p. 967,2001.

Iwatani, "An Estimation Method of Skin Blood Flow Rate Using Heat Flow Analysis," *Japanese Journal of Medical Electronics and Biological Engineering*, vol. 20, No. 3, pp. 249-255, includes English Abstract, 1982.

Levine et al., "Face of Fear", *The Lancet*, vol. 357, No. 9270, Jun. 2, 2001.

Pavlidis et al., "Automatic Detection of Vehicle Occupants-The Imaging Problem and Its Solution," *Machine Vision and Applications*, vol. 11, No. 6, pp. 313-320, 2000.

Pavlidis et al., "Monitoring of Periorbital Blood Flow Rate Through Thermal Image Analysis and its Application to Polygraph Testing", Proceedings 23rd Annual International Conference of the IEEE Engineering in Medicine and Biology Society, Instanbul, Turkey, Oct. 25-28, 2001.

Pavlidis et al., "Thermal Imaging for Anxiety Detection", 2000 *IEEE Workshop on Computer Vision Beyond the Visible Spectrum: Methods and Applications*, pp. 104-109, Hilton Head Island, South Carolina, Jun. 16, 2000.

Measuring Intelligence. www.bbc.co.uk/science/hottopics/intelligence/iq.shtml. Apr. 2002.

\* cited by examiner

DETECTION SYSTEM AND METHOD USING THERMAL IMAGE ANALYSIS

CROSS-REFERENCE TO RELATED APPLICATIONS

This application claims the benefit of U.S. Provisional Application No. 60/210,279, entitled "Detection system and method using thermal image analysis," filed 8 Jun. 2000, wherein such document is incorporated herein by reference.

BACKGROUND OF THE INVENTION

The present invention relates generally to detection systems and methods using thermal analysis. More particularly, the present invention pertains to the detection of physiological response characteristics representative of one or more altered human states, e.g., anxiety, alertness, fear, depression, etc., using thermal analysis systems and methods.

In many situations, detection of individuals is very important. For example, in high-end security applications, e.g., surveillance of an embassy perimeter where there is a need to know who certain individuals are within a particular setting and/or what individuals are about to do within a particular setting, detection of individuals is required. Further, for example, such detection systems and methods may not only be required in high-end security situations, but may also be needed in government buildings, schools, airports, and border control points. As such, systems for early detection and identification of individuals, e.g., detection at a distance, need to be developed and implemented.

Generally, certain recent biometric technologies (e.g., such as face recognition systems that may be able to match prestored data regarding a particular individual to real time collected data of an individual) have been developed which may be used in situations such as those described above. However, such systems have problems when employed in a realistic setting (e.g., outside a U.S. embassy). For example, many face recognition systems are only applicable to repeat offenders with archived facial pictures. As such, these systems cannot address the case of a person in a security setting who has a clear record, or no record, that appears for the first time in a critical facility or any other civilian facility (e.g., an airport), and who may be attempting to do either harm or smuggle harmful materials. For example, a foreign national may not be captured when trying to smuggle explosives into the country as the foreign national may not have a record. However, an immigration officer with an experienced eye can detect an anxious state of such an individual who has no record and initiate an examination of the individual's belongings. Generally, alertness, anxiety, and even fear, accompany such people who are involved in terrorist or harmful activities at the time of their action.

Traditional human identification systems, in circumstances such as those described above, generally seek to detect an answer to the question, "Who are you?" Thereafter, upon determining who the person is, the potential of such an individual's risk is then based on the identification of the person. However, as described above, the identification of such persons may not be possible or may at least be problematic, e.g., the problematic identification of a person with no record. As such, when persons cannot be effectively identified, the risk posed by such an individual cannot be determined.

SUMMARY OF THE INVENTION

Various embodiments of the present invention provide solutions to one or more problems existing with respect to detection systems and methods currently available. For example, the methods and systems according to the present invention focus on the question, "What are you about to do?" as opposed to "Who are you?" in the determination of an individual's risk. As such, the methods and systems may be used alone or in combination with other traditional biometric products, such as face recognition systems, in multiple applications including security applications, such as for government buildings, schools, airports, and border control points. The present invention provides for thermal image analysis to detect physiological response characteristics of human states, e.g., anxiety, depression, etc.

The present invention capitalizes on the fact that physiological response symptoms of anxiety are produced by the sympathetic system of the human being which cannot be totally controlled thereby. Therefore, such symptoms which are detectable using thermal image data can provide valuable information as to the physiological state of the person. Some embodiments of the methods according to the present invention include one or more of the following: providing thermal image data of at least a region of a face of a person; using thermal image data to determine a physiological state of a person; using thermal image data to determine anxiety in a person; using thermal image data of at least a region proximate an eye of the person, e.g., the periorbital region proximate the eye of a person, to determine a physiological state of a person; comparing the thermal image data to a baseline reference to determine a physiological state of a person; comparing thermal image data of a periorbital region of the person to thermal image data of another region of the person's face to determine a physiological state of the person (e.g., a cheek region of the face); providing thermal image data of at least a region of the face of a person by providing thermal image data of a scene and thereafter selecting the thermal image data of the face from the scene; and providing thermal image data of the face of the person and thereafter identifying thermal image data for one or more regions of the face based on at least bilateral symmetry of the thermal image data of the face.

Some embodiments of a detection system to detect a physiological state of a person include one or more of the following features: a thermal infrared image device operable to provide thermal image data of at least a region of the face of a person; circuitry (e.g., specialized hardware or processing circuitry executing software) operable upon thermal image data to determine a physiological state of a person; circuitry operable upon thermal image data to determine the presence of anxiety in a person; a thermal infrared image device operable to provide thermal image data of at least a region proximate an eye of the person; circuitry operable to compare the thermal image data to a baseline reference; circuitry operable to compare thermal image data of a periorbital region to thermal image data of another region of the face (e.g., a cheek region of the face); a thermal infrared image device operable to provide thermal image data of a scene such that the circuitry is operable thereon to select thermal image data of the face of a person from the thermal image data of the scene; and circuitry operable to identify thermal image data for one or more regions of the face based on at least bilateral symmetry of the thermal image data of the face.

BRIEF DESCRIPTION OF THE EMBODIMENTS

DETAILED DESCRIPTION OF THE EMBODIMENTS

Figure 1:
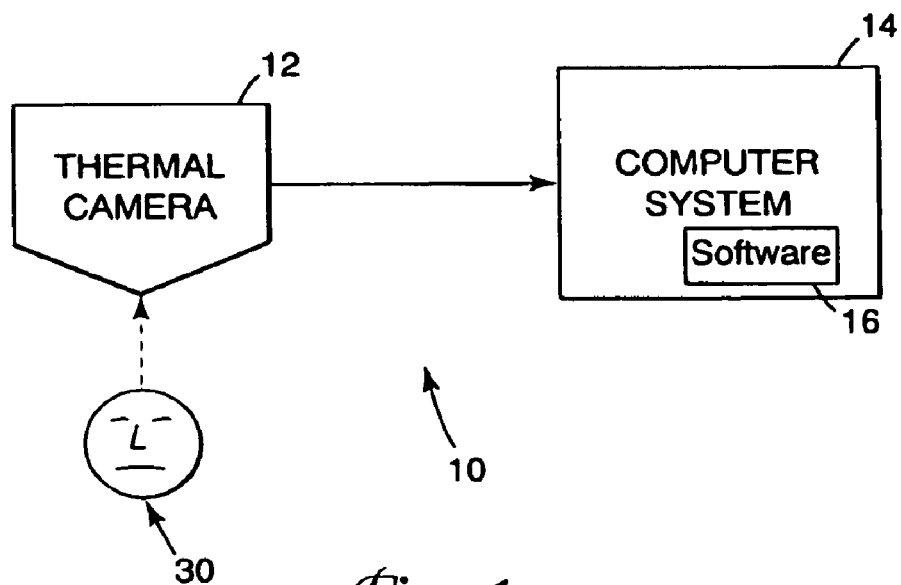
FIG. 1 is a block diagram illustrating one exemplary embodiment of a physiological state detection system according to the present invention.

The present invention shall be described with reference to FIGS. 1–7. Generally, the present invention detects a physiological state of a person through the analysis of thermal image data of at least a region of a face thereof. The method and system described herein may be used to determine one or more different physiological states of a person. For example, depression, periods of dementia, anxiety, etc. However, for simplicity purposes, the remainder of the description herein shall be provided with reference primarily to determining an anxiety state of a person.

As used herein, and in interest of brevity, the term anxiety shall identify a set of feelings. This set of feelings includes alertness, anxiety, fear, and the like. Such a set of feelings are generally symptomatic in individuals at the time individuals are engaged in certain activities, such as terrorist or illegal activities. Such feelings or symptoms are produced by the sympathetic system and cannot be totally controlled by the person. As such, they provide a biometric indicator, e.g., measurable physiological response, that is extremely difficult to conceal. This biometric can provide valuable clues in many circumstances, such as, for example, to security personnel of critical facilities wherein potential suspects may be "immune" to identification biometrics (e.g., first time offenders for whom no facial record is available). Systems and methods based on such a biometric can be used to prevent serious security issues, such as, for example, the smuggling of narcotics at border control points, terrorists at foreign facilities, etc. Such a system and method could be used to identify potential offenders allowing authoritative personnel to intervene on a selective basis.

In general, the present invention relies on the change in the thermal facial image signature of an individual when the individual is experiencing anxiety. According to at least one embodiment of the present invention, anxiety is accompanied by an increased local warming around the individual's eyes. This change in facial thermal pattern around the individual's eyes is typically accompanied by concomitant cooling over the cheeks and/or concomitant warming over the carotid artery regions. Further, typically, the mean temperature of the nasal area remains unchanged.

Generally, this pattern of thermal change in an individual's body during an onset of anxiety (e.g., the change in the individual's thermal signature during onset of anxiety) makes physiological and evolutionary sense as it represents a mechanism to facilitate rapid eye movement during preparedness for flight. In other words, elevated anxiety precipitates a host of physiological responses, many of which result from altered sympathetic nervous system activity. One of these responses is local redistribution of blood flow resulting in abrupt changes in local temperatures at various regions in the individual. Such changes in local temperatures in such regions are readily apparent in the human face where the layer of flesh over bone is relatively thin.

Such abrupt temperature changes in localized regions can be detected by human face emissions in both the mid-infrared thermal band (i.e., 3 microns to 5 microns band) and far-infrared thermal band (i.e., 8 microns to 14 microns band) of the electromagnetic spectrum. One skilled in the art will recognize that slightly shorter or longer ranges can also yield acceptable detection results. For example, with respect to the ranges given above, a deviation from such wavelength values which may produce acceptable detection results is contemplated to fall within the specified ranges.

Figure 2:
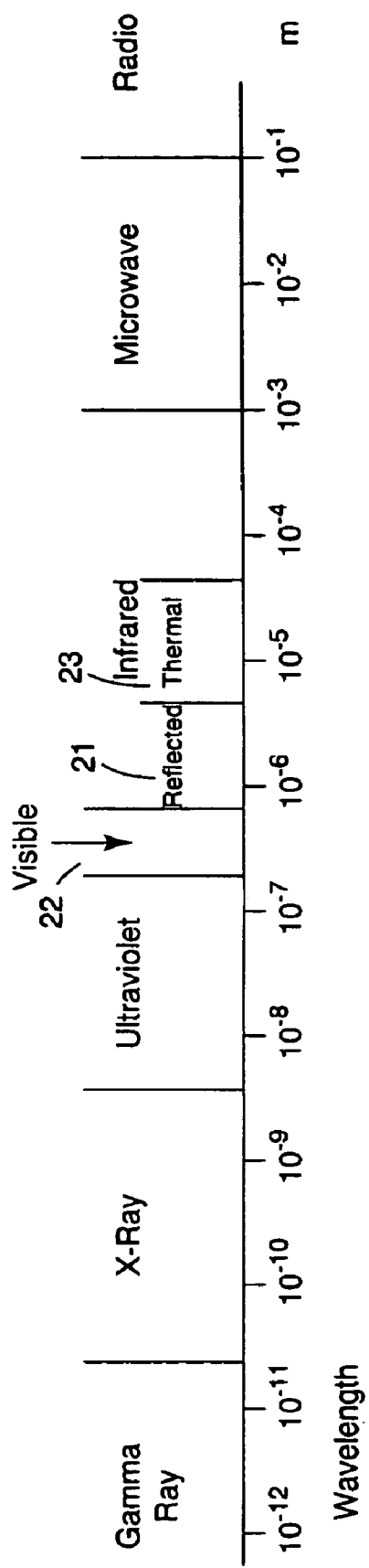
FIG. 2 is a graph of the electromagnetic (EM) spectrum.

A graph of the electromagnetic spectrum is shown in FIG. 2, with the thermal infrared band shown as reference numeral 23. The thermal infrared band lies above the visible band 22 and reflected infrared band 21 of the electromagnetic spectrum. As such, thermal infrared detectors suitable to sense temperature variations in such regions of the spectrum can be used to produce thermal facial images, or thermograms, representative of such local temperature changes in the human face of an individual. Such data of the thermograms (e.g., those using either one or both of the mid-infrared band and far-infrared band) may be used to determine a physiological state of the individual, e.g., anxiety.

It will be readily apparent that different activities will produce distinct, non-overlapping facial thermal patterns. Therefore, the detection of these activities using such facial thermal patterns may be performed either through observation or operation of an algorithm upon the thermal image data, e.g., machine vision algorithm that uses optical non-contact sensing to automatically provide and interpret an image of a real scene to obtain information therefrom (e.g., the existence of anxiety in an individual in the scene). Although, as described above, various different physiological states resulting from activities of the individual may be detected, the present invention shall be described further below with respect to the thermal facial imagery of anxiety.

As described above, and as shown with reference to FIG. 3, a thermal facial image of an individual 30 with reference to various regions of the individual's face 32 shall be described that provides an individual's signature that can be detected as anxiety. As mentioned earlier, an onset of anxiety in the individual 30 (e.g., such as may be induced by a startling stimulus, induced by fear when smuggling goods into the country, induced by fear arising from the need to establish an escape route when proceeding with covert operations in a secret area, induced by lying, etc.) is associated with a warming due to increased blood flow in the periorbital region 34a–b around the eyes 35. The periorbital region size will vary with the individual. This extra blood flow to the eye musculature in the periorbital region 34a–b is primarily redirected from the cheek regions 36a–b, indicated by a cooling in such cheek regions 36a–b. Further, some of the additional blood flow may be coming from the rest of the body as indicated by the warming of the carotid vein region 40a–b in the neck 41 of the individual 30. Also, as indicated previously, the thermal properties of the nasal region 42a–b remain substantially unchanged during an onset of anxiety. One skilled in the art will recognize that one or more other parts of the face, e.g., chin, may be used in addition to those previously listed, or as an alternative to those previously listed, for the determination of anxiety.

With the abrupt changes in temperature in the localized regions of the individual's face 32 that accompany an onset of anxiety, and with suitable monitoring of emissions from the individual 30 in the thermal infrared spectrum from before the time of anxiety onset (e.g., a thermal history) and also after the time of onset, detection of the transition from a prior state (e.g., a calm state) to an anxiety state can be achieved. This change in facial thermal infrared pattern or signature at the time of the transition is dramatic and can be easily recognized.

However, in many situations, to have the thermal history of the subject individual being monitored (e.g., an individual under surveillance) is unlikely. Therefore, individuals who appear anxious, e.g., those in and about critical installations to perform terrorist activities, will already be in an anxious state. As such, detection based on a transition from a prior state to an anxiety state is not possible due to the lack of such thermal history of the individual. Therefore, to detect anxiety in such individuals, a baseline for the thermal signature of individuals in an anxiety state across the human race is necessary. With such a baseline of thermal symptoms or features, a comparison can be made between the baseline and acquired thermal infrared facial image data such that one can classify an anxious individual from a non-anxious individual at any point in time without any prior knowledge of the individual's thermal history.

In view of the preceding generalities, an illustrative embodiment of a physiological state detection system 10 according to the present invention shall be described. In conjunction with this detection system 10, preferably, various software routines or algorithms 16 are generally described for carrying out various steps of multiple embodiments of a detection method for determining a physiological state of an individual.

The physiological state detection system 10, e.g., for determining a state of anxiety in an individual 30, is generally illustrated in FIG. 1. The detection system 10 includes a thermal infrared image device 12 operable to provide suitable thermal image data representative of a scene in which individual 30 (see FIG. 3) is located. The thermal image data from the thermal infrared image device 12 is provided to circuitry 14.

Preferably, circuitry 14 includes a computer system operable to execute software 16 to provide for the determination of a physiological state, e.g., anxiety, based on thermal image data. Although the circuitry 14 may be implemented using software 16 executable using a computer apparatus, other specialized hardware may also provide the functionality required to provide a user with information as to the physiological state of the individual 30. As such, the term circuitry as used herein includes specialized hardware in addition to or as an alternative to circuitry such as processors capable of executing various software processes.

The computer system, which shall be referred to hereinafter with reference numeral 14, may be, for example, any fixed or mobile computer system, e.g., a personal computer or a minicomputer. The exact configuration of the computer system is not limiting and most any device capable of providing suitable computing capabilities may be used according to the present invention. Further, various peripheral devices, such as a computer display, a mouse, a keyboard, memory, a printer, etc., are contemplated to be used in combination with a processing apparatus in the computer system 14.

The thermal infrared image device 12 is preferably one or more thermal cameras having pixel arrays sensitive to the mid-infrared and/or far-infrared bands of the electromagnetic spectrum. For example, the thermal infrared image device 12 may be an uncooled thermal camera sensitive in the far-infrared band (i.e., the 8 micron to 14 micron band) available from Raytheon and provided under the trade designation ExplorIR. Further, for example, the thermal infrared image device 12 may be a mid-infrared camera sensitive in the mid-infrared band (i.e., the 3 micron to 5 micron band) available from Raytheon under the trade designation Radiance HS Mid-Infrared Camera. As indicated previously, the human body and face emit in both the mid-infrared and far-infrared bands of the electromagnetic spectrum. Therefore, preferably, both a far-infrared camera and a mid-infrared camera are used to provide thermal image data such that the data in the far-infrared band and the mid-infrared band may be compared to provide additional accuracy. However, one skilled in the art will recognize that either one or both of a far-infrared band and/or mid-infrared band camera may be used according to the present invention. Further, it is preferred that highly sensitive cameras be used when attempting to detect subtle changes in physiological response.

The far-infrared camera provided under the trade designation ExplorIR has a nominal temperature sensitivity of noise equivalent temperature difference (NETD) equal to 0.15° C. However, such performance is typically not obtained and the actual temperature sensitivity of the ExplorIR model may be above 0.5° C. As this is only a fair amount of facial temperature resolution, a certain amount of information may be masked thereby. The mid-infrared camera available from Raytheon under the trade designation Radiance HS Mid-Infrared Camera is specially calibrated with nonlinear equations for improved accuracy. It generally has an NETD equal to 0.025° C. A calibration process may be complemented with a smart, highly accurate (0.01° C.) differential black body for near perfect scene temperature reference.

The computer system 14 includes software components 16 for analysis of thermal facial images provided from thermal infrared camera 12. One or more of such software components 16 may be used to operate on the thermal image data, e.g., pixel data, provided from the thermal infrared camera 12 to determine whether an individual 30 is in an anxiety state. Such algorithmic software components for analysis of the thermal facial images of an individual 30 are shown as a part of an exemplary block diagram of an anxiety detection method 60 in FIG. 4.

Figure 4:
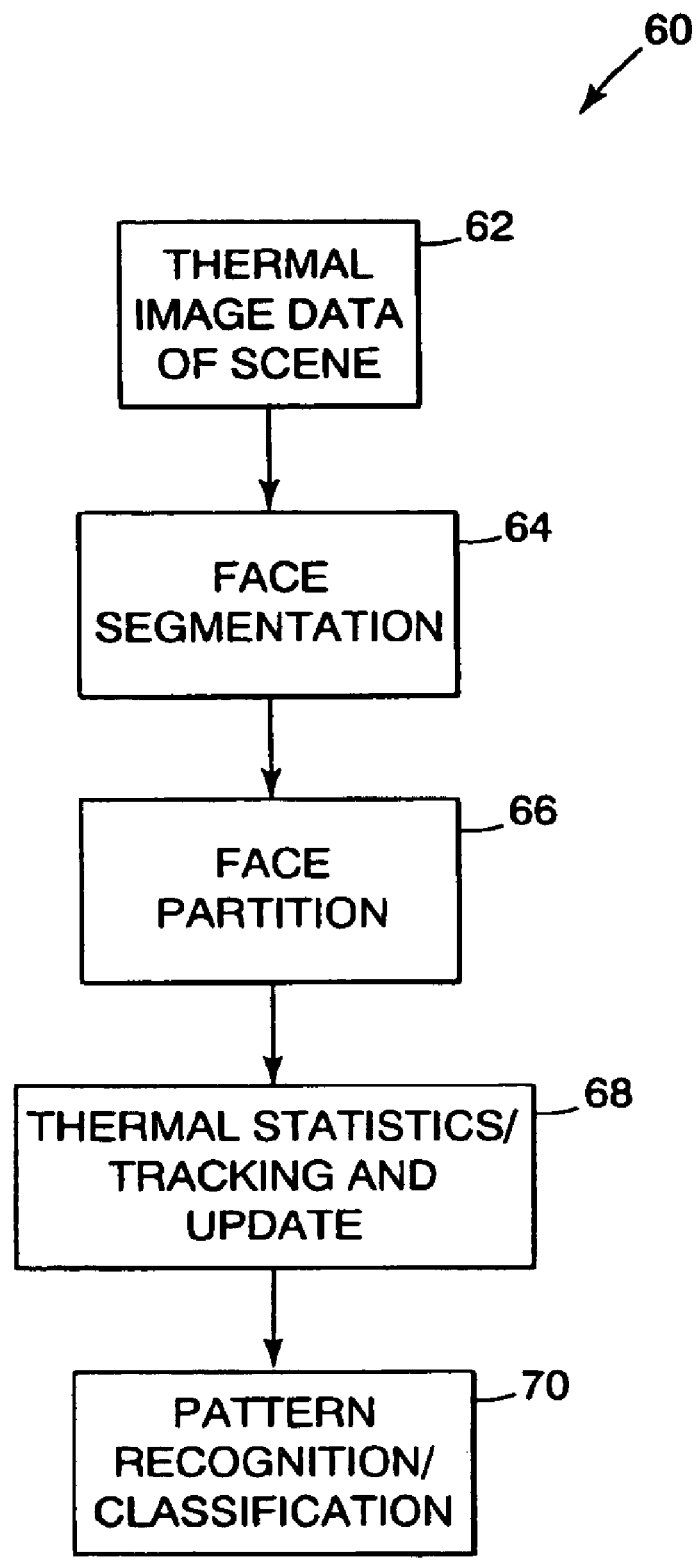
FIG. 4 is a block diagram illustrating the flow and operation of multiple algorithmic software components used for analysis of thermal image data according to the present invention.

As shown in the anxiety detection method 60 of FIG. 4, thermal image data 62, e.g., pixel data, of a scene in which individual 30 is located is provided to the computer system 14 and is thereafter operated upon by software components 16. Such software components include a face segmentation component 64, a face partition component 66, a thermal statistics tracking and update component 68, and a pattern recognition/classification component 70. One or more of such components may be used in determining an anxiety state of the individual 30 based on the thermal image data provided from thermal infrared camera 12. However, it will be recognized that not all of such software components 16 need be used to perform such an analysis.

Figure 3:
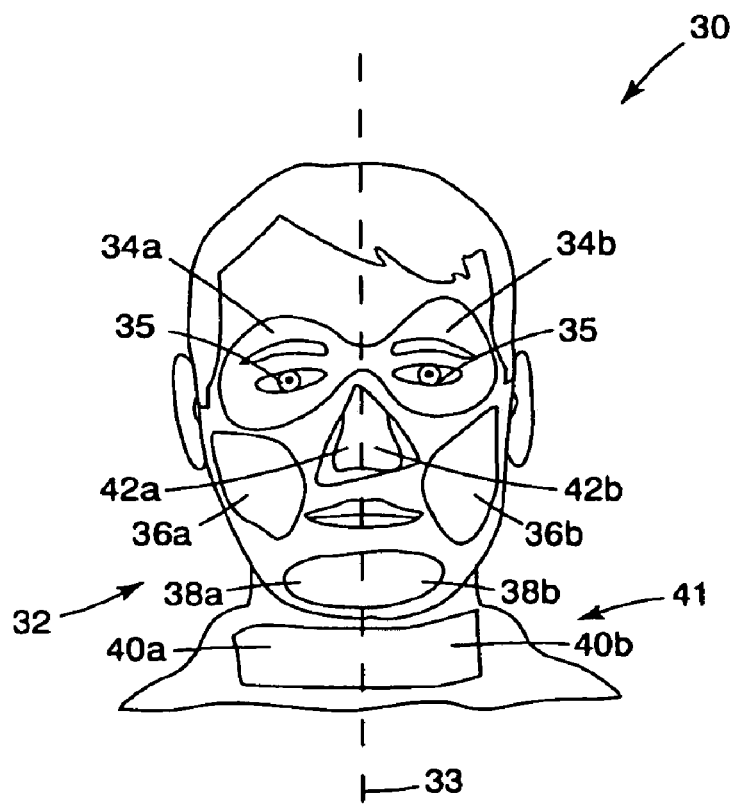
FIG. 3 is a diagram of an illustrative thermal facial image showing partitioned regions according to the present invention.

Generally, face segmentation component 64 provides a segmentation algorithm to separate thermal image data of the face 32 from the background of the thermal image data of the scene provided from camera 12 in block 62. The face partition component 66 provides an algorithm to partition the thermal image data of the face 32 into one or more regions. In one exemplary embodiment as shown in FIG. 3, the one or more regions may include five areas or regions: the periorbital region 34a–b; the nasal region 42a–b; the cheek region 36a–b; the chin region 38a–b; and the neck region (or otherwise referred to as the carotid region) 40a–b.

Further, generally, the thermal statistics tracking and update component provides for the tracking of regional thermal statistics (e.g., thermal data representative of pixels in one or more of such partitioned regions) for one or more regions of interest. In other words, this tracking and update component 68 performs a monitoring function which may update the regional thermal data dynamically from frame to frame grabbed by the thermal infrared camera 12.

Lastly, in general, pattern recognition/classification component 70 may provide a pattern recognition algorithm operable upon thermal data representative of one or more of the partitioned regions of the face. For example, automatic classification of the individual 30 into an anxiety existing versus a non-anxiety existing classification may be performed. Preferably, the pattern recognition algorithm is an algorithm that is part of a class of algorithms using statistical learning methodology. This may be used to correct for some variability in the thermal signatures across the human race.

Therefore, generally, the anxiety detection method 60 includes the provision of thermal image data of a scene (block 62). The thermal image data of the scene is processed such that the thermal image data of the face 32 of the individual 30 is segmented from the background of the scene (block 64). Thereafter, the thermal image data of the face is partitioned into one or more regions, e.g., periorbital region, cheek region, etc. (block 66). The thermal image data is then monitored (block 68) such that it may be subsequently used to classify or identify the individual as having anxiety or not having anxiety (block 70).

Figure 5B:
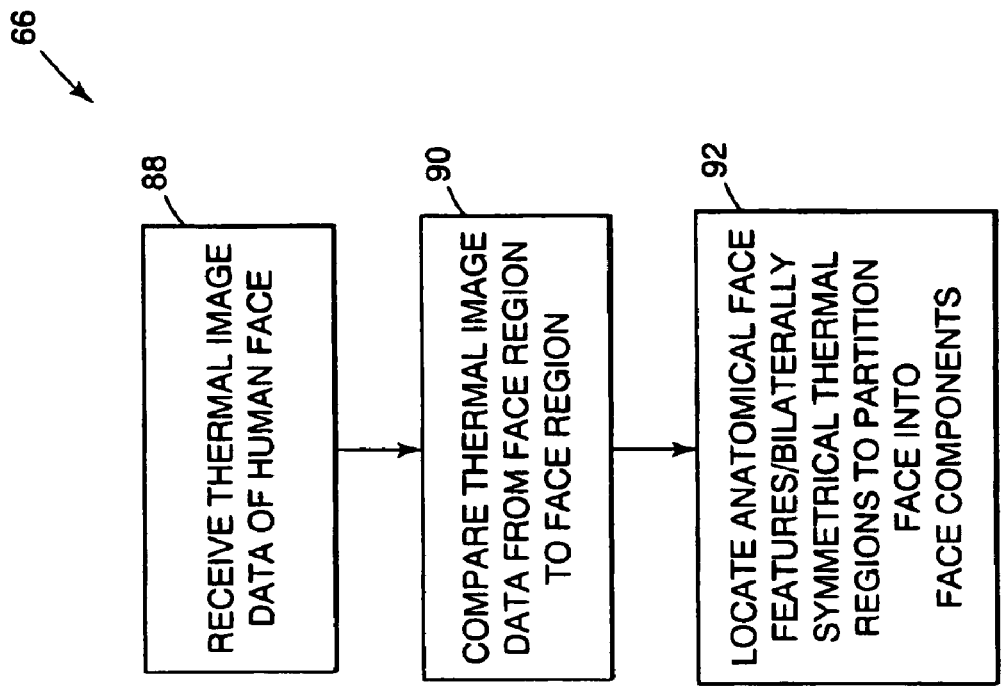
FIG. 5B is one illustrative block diagram of an exemplary face partition component as shown in FIG. 4.
Figure 5A:
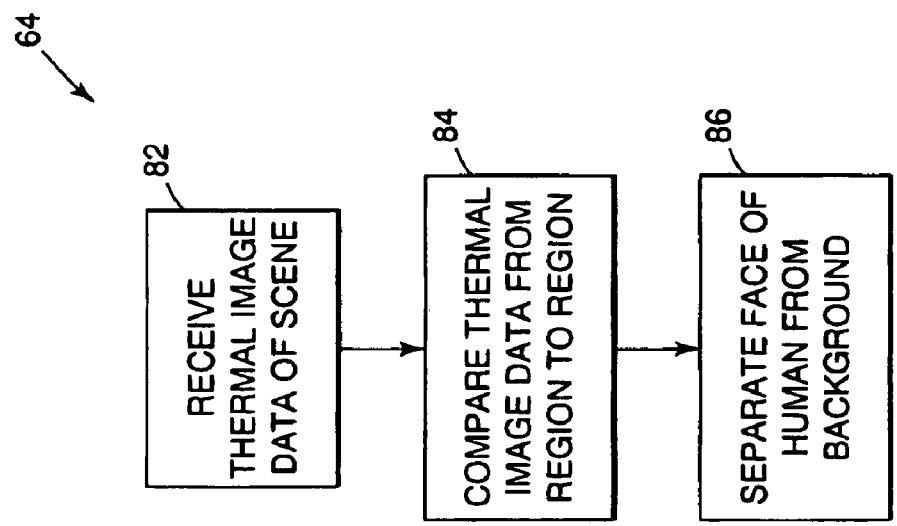
FIG. 5A is one illustrative block diagram of an exemplary face segmentation component as shown in FIG. 4.

FIG. 5A is one illustrative embodiment of an exemplary process performed using the face segmentation component 64 of the software component 16 for use in detection of anxiety in the individual 30. As shown therein, thermal image data of a scene is received (block 82) from the thermal camera 12. Such information includes pixel data of one frame of the scene.

The pixel information may be either in the form of digital values or direct temperature readings. Of course, the digital values are proportional to the actual scene temperatures at the respective points or pixels. In other words, pixel values have either indirect or direct correlation to scene temperatures. This is in contrast to visible band images, where pixel values have direct correlation to reflectance values.

Such received thermal image data representative of the thermal characteristics in the scene may be directly displayed and/or stored by the computer system 14. For example, software associated with the computer system 14 may allow for the direct display of such data in degrees centigrade. For example, in many commercial systems, such data may be provided in gray scale values. Such gray scale display of images may generally have a poor visualization effect. Other commonly employed rainbow pseudo-coloring display schemes may have relatively better imaging quality but achieve optimal results for the dynamic range of the visible band of the electromagnetic spectrum. Although such methods of display may be used, preferably a pseudo-coloring technique geared toward the optimal display of thermal infrared image data is used.

Figure 7:
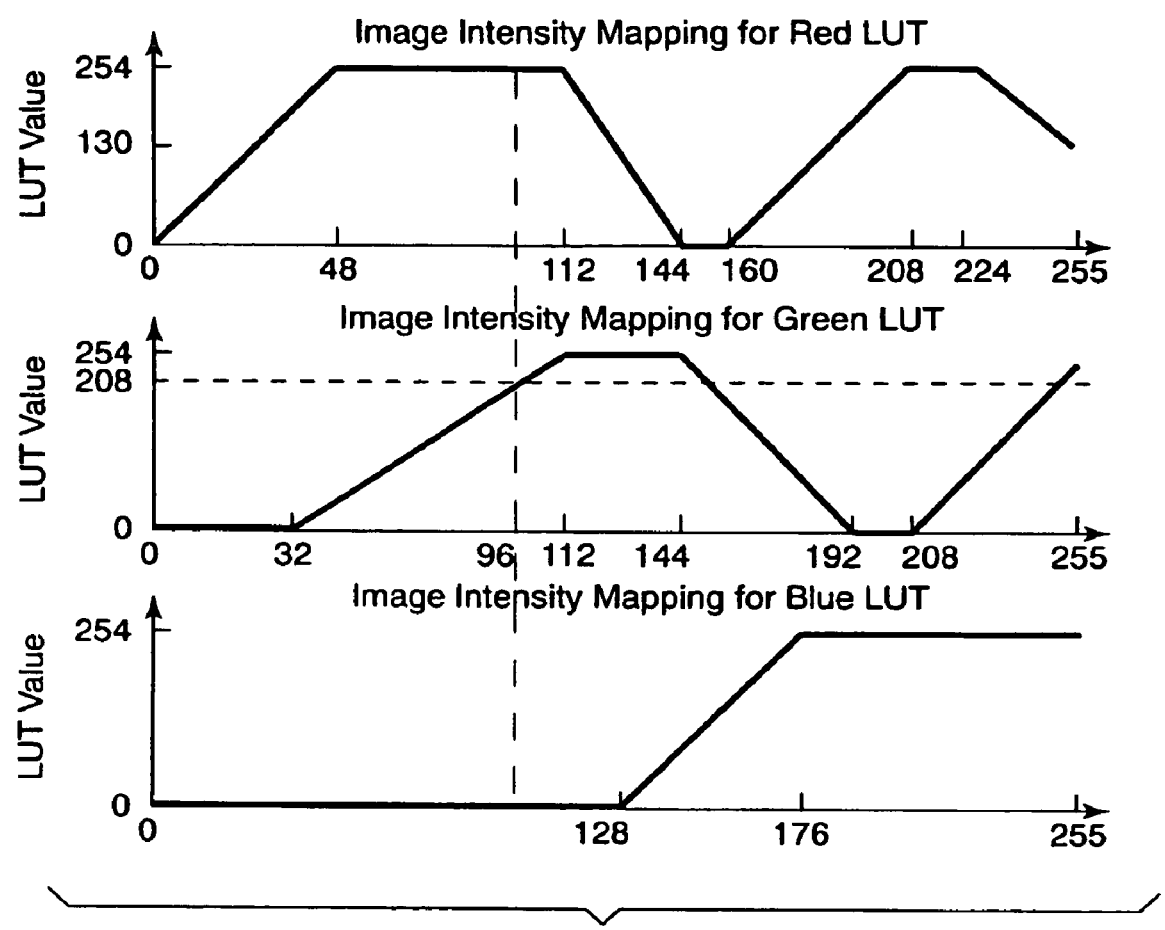
FIG. 7 is an image intensity mapping diagram used in describing an exemplary pseudo-coloring scheme according to the present invention.

One exemplary pseudo-coloring technique preferred according to the present invention makes contrast between warmer and cooler regions of the face more distinct, therefore, leading to more effective visualization. As shown in FIG. 7, red, green, and blue are mapped according to the shown graphs. For example, a certain amount of red is displayed, a certain amount of green is displayed, and a certain amount of blue is displayed, depending upon the digital value for the pixel representative of the temperature thereof. For example, as shown in FIG. 7, for digital value 96 as shown along the horizontal axis, no blue is displayed, a quantity of green corresponding to the look up table (LUT) value 208 is displayed, and as much red as possible is displayed. One skilled in the art will recognize that patterns of the graphs shown in FIG. 7 are of one preferred embodiment of the mapping of the various colors. However, other schemes may also be used to provide a particularly distinct visualization between warmer and cooler regions.

The thermal image data of the scene is then operated upon to compare thermal image data from at least one region of the scene to thermal image data of another region of the scene. As the thermal characteristics of the human face are usually well contrasted to those of the background, such a comparison (block 84) can be easily implemented. This comparison results in data which can be used to separate the human face from the background (block 86). The thermal image data of the human face separate from the background can then be used by the face partition component 66 which partitions the human face into one or more regions of interest.

FIG. 5B shows one illustrative embodiment of an exemplary method performed by face partition component 66. The face partition component 66 receives thermal image data of a human face (block 88) from the face segmentation component 64. Generally, the face partition component 66 then segments the human face into the one or more regions of interest. Preferably, as shown in the method of FIG. 5B, and preferably according to one particular embodiment of the present invention which detects a level of anxiety in the individual 30, the human face is segmented into five regions of interest. Such regions of interest were previously defined herein as the periorbital region 34a–b, nasal region 42a–b, cheek region 36a–b, chin region 38a–b, and neck region (or carotid region) 40a–b.

To provide for segmentation of the face, thermal image data from one region of the face is compared to thermal image data of another region of the face (block 90) to distinguish the particular regions from each other for segmentation. The underlying anatomical features of the face 32 facilitate locating and orientating the face 32 for segmentation and analysis. For example, as shown in FIG. 3, the face 32 is bilaterally symmetrical about plane 33 (defined through the face 32, e.g., orthogonal to the FIG. 3) and aids segmentation into regions of interest, e.g., one eye in each half of the face, the nose lying half on one side of the plane 33 and half on the other side of the plane, etc. As such, generally, there is also symmetry of thermal image data from one side of the face to the other side. For example, variation in temperature from hot areas on either side of the nasal region 42a–b to the relatively cool areas of the ears and cheeks are symmetrical about plane 33. The eyes 35 themselves (not the eye musculature) always appear cooler relative to the neighboring areas, e.g., the periorbital regions 34*a–b*. From the symmetrical variation of temperature about plane 33 and the structure of the face itself, e.g., eyes, mouth, ears, etc., the regions of interest may be isolated and thermal image data relative to such regions determined. Such bilateral symmetry is shown by regions 34*a*, 36*a*, 38*a*, 40*a* and 42*a* on the left side of the plane 33 and regions 34*b*, 36*b*, 38*b* 40*b*, and 42*b* on the right side of the plane 33.

One can achieve demarcation of the facial regions using various algorithmic methods. For example, a region competition algorithm derived by minimizing a generalized Bayes/MDL criterion using a variational principle may be used for such demarcation of the facial regions. Such algorithms are described in an article by S. C. Zhu and A. Yuille, entitled "Region Competition: Unifying Snakes, Region Growing, and Bayes/MDL for Multiband Image Segmentation," IEEE Transactions on Image Analysis and Machine Intelligence, Vol. 18, No. 9 (September 1996).

Preferably, the segmentation algorithms should be able to perform on static images as well as on a dynamic sequence of images, e.g., video clips, live video feeds, etc. Although a single image may be used for detection purposes according to the present invention, a sequence of images is preferably acquired for such detection purposes. As such, in the case of image sequences, e.g., dynamic image sequences provided in a real-time fashion, the thermal statistics tracking and update component 68 is used to lock onto the face and one or more of the segmented or partitioned regions of interest on the face. Such segments or regions of interest may then be tracked from frame to frame with a change in anxiety level being noticed or identified immediately.

Further, data from the multiple images may be used to provide accurate and effective thermal image data of one or more of the partitioned regions of interest of the face. The thermal data of one or more regions of interest, e.g., the periorbital region, the cheek region, etc., provide information that can be used for classification by the pattern recognition/classification software component 70. In other words, the thermal statistics/tracking and update software component 68 continuously locks onto the face and the segmented regions of interest therein from frame to frame throughout a period of time. The thermal data of one or more of the regions obtained throughout this dynamic tracking can be updated dynamically from frame to frame to provide the necessary thermal data for classification.

The software components 64, 66, and 68, either together or just one or more of them, operate as the pre-processing routines that provide the thermal image data to pattern recognition/classification software component 70. As described previously herein, such classification may be performed manually by a person viewing thermal facial images on a display. For example, as previously indicated herein, if a person without anxiety is present within the scene, a certain thermal image signature will be apparent on the display. However, if that person develops anxiety while in the scene and as a user is watching the display, the individual's thermal facial image signature will change dramatically and the user can manually classify the individual as in an anxiety state. As such, the pattern recognition/classification software component 70 may be implemented through software that displays the thermal facial images of the human face to a user, e.g., the pseudo-coloring technique.

However, preferably, the pattern recognition/classification software component 70 performs automatic classification into anxiety and non-anxiety states. Preferably, the algorithms of the software component 70 operate in a training and performance mode. For example, in the training mode, the software component may include algorithms that belong to the class of statistical learning methodology such as described in M. I. Jordan and R. A. Jacobs, entitled "Hierarchical Mixtures of Experts and the E M Algorithm," Neural Computation, Vol. 6, pp. 181–214 (1994). In such a training mode, as the routine learns about the statistical thermal data with regard to individuals in an anxiety state, algorithms can be updated and the accuracy of such classification will become more reliable. In the performance mode, the algorithm operates to perform the actual classification.

Figure 6:
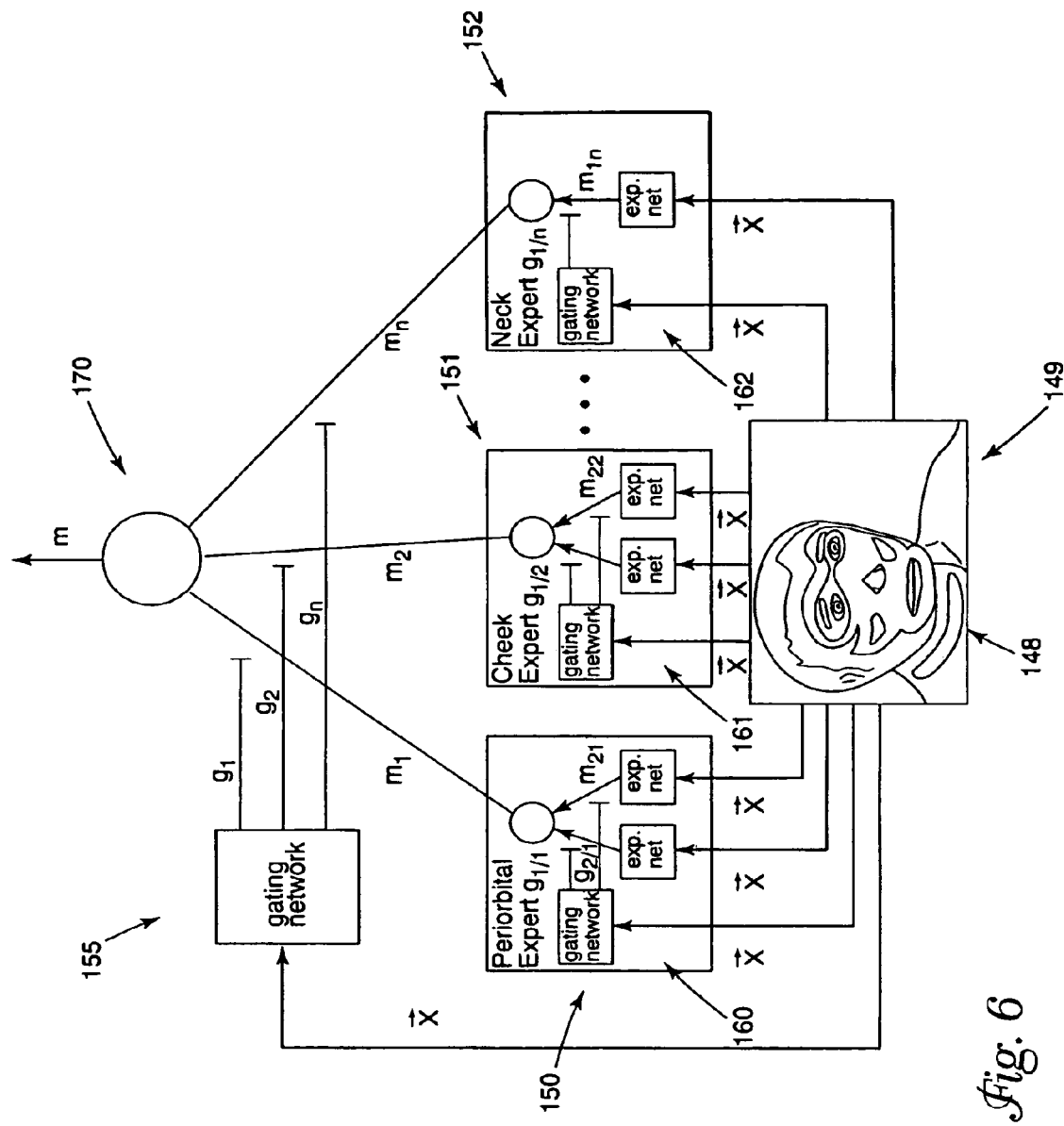
FIG. 6 is an illustration of a learning architecture for detecting human anxiety.

One exemplary learning architecture is shown in FIG. 6 for detecting human anxiety via processing of thermal statistics data associated with certain facial regions. The learning architecture encompasses the principle of divide and conquer and is realized by a Hierarchical Mixture of Experts (HME) model, such as described in the Jordan et al. article cited above. In this model, learning is considered a maximum likelihood problem and an Expectation-Maximization (EM) algorithm is used to adjust the learning parameters. The architecture uses a set of local experts 150–152. Each of the local experts 150–152 evaluates certain aspects of the input data 149. The contribution of certain input data to the decision of the local expert is weighted through a gated network 160–162 associated with each of the local experts 150–152, respectively. The contribution of the local experts 150–152 to the final decision 170 is weighted through a gated network 155. Detection of anxiety maps naturally into this architecture where the local experts 150–152 are associated with particular facial regions 148, e.g., nasal region, cheek region, etc. The local experts 150–152 evaluate thermal statistical characteristics in cooperation with the segmentation algorithms for the regions. Thereafter, a gating network learns the association of these thermal statistics with the state of human anxiety.

Figures 5C, 5D:
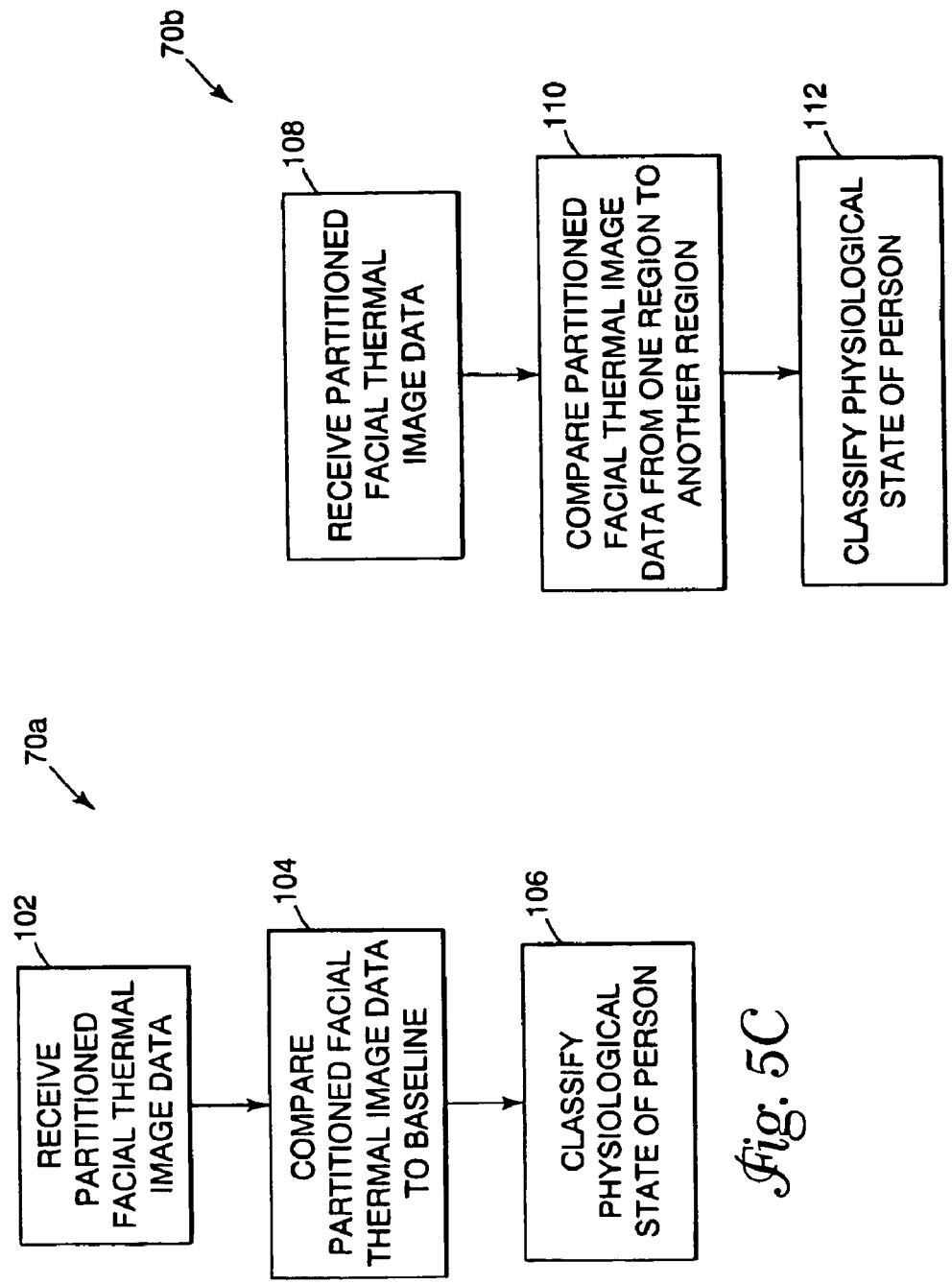
FIG. 5C is one illustrative block diagram of an exemplary pattern recognition/classification component as shown in FIG. 4.
FIG. 5D is another illustrative block diagram of an exemplary pattern recognition/classification component as shown in FIG. 4.

FIGS. 5C and 5D show exemplary methods 70*a–b* that may be performed by pattern recognition/classification software component 70. The classification method 70*a* uses comparison of thermal facial image data to a determined baseline to perform such classification, whereas the classification method 70*b* uses a comparison of thermal facial image data from one partitioned region of the human face to another partitioned region of the human face to perform such classification.

As shown in FIG. 5C, the classification method 70*a* includes receiving partitioned facial thermal image data (block 102) from the pre-processing software components described above, e.g., components 64, 66, and/or 68. The thermal image data from one or more of the partitioned regions of the face 32 is then compared to a baseline reference (block 104). This comparison is then used to classify the physiological state of the person (block 106), e.g., classify the individual 30 as being in an anxiety state or in a non-anxiety state.

The baseline reference may, for example, be a baseline of an anxiety-induced thermal facial image or signature. For example, statistical analysis may be used to develop a baseline for an individual in a non-anxiety state and thereafter in an anxiety state. Various thermal response variabilities across the human race must be considered. In other words, the state of anxiety may be shown by varied thermal facial images depending on various factors. For example, the mental state of the individual, the intelligence of an individual, the race of an individual, the physical conditioning of an individual, the blood pressure of an individual, and many other variables across the human population will effect the thermal facial image of an individual in an anxiety state.

In addition, other conditions relative to obtaining a thermal facial image from an individual must also be considered. For example, the effect of environmental conditions on acquisition of thermal facial images must be considered. Such environmental conditions may include the effect of temperature, the effect of light on the scene, the effect of wind at the scene, as well as other environmental conditions. As such, with collection of experimental data and analysis thereof, a baseline reference covering a large population may be determined.

Once a baseline reference is set, e.g., such as for a particular partitioned region (e.g., periorbital region) of the face, then thermal image data acquired for such a region can be compared to the baseline reference. For example, thermal image data may be acquired and processed for the periorbital region of an individual. Thereafter, the thermal data for the periorbital data can be compared to a threshold level based on the reference developed for an individual in an anxiety state. If the thermal image data satisfies the threshold then the individual can be classified in an anxiety state.

The classification method 70b, as shown in FIG. 5D, also includes the receipt of partitioned facial thermal image data (block 108) from one or more pre-processing software components 64, 66 and/or 68. However, as opposed to comparison of the data to just a baseline reference as described with reference to FIG. 5C, rather a comparison is made between the thermal image data from multiple regions of interest of the human face 32, e.g., a ratio of an average thermal state of one region to another. Such a comparison of data is then analyzed, e.g., by comparison, to a reference level or threshold developed in much the same manner as described above and used to classify the physiological state of the person (block 112), e.g., classification of the individual 30 as being in an anxiety or non-anxiety state.

For example, in accordance with the method shown in FIG. 5D, facial thermal image data may be selected for the periorbital region 34a–b and the cheek region 36a–b. The thermal image data from such regions may be compared to one another, e.g., a difference or a ratio, and then analyzed, e.g., by comparison with a threshold, to determine the state of anxiety of the individual 30. Although various regions of the human face may be used to determine the state of anxiety, preferably, a comparison between at least the periorbital region and another region of the face is used because of the significant temperature change in the periorbital region 34a–b of the human face 32. Further, because there is an increase in temperature of the periorbital region 34a–b using blood flow from the cheek region 36a–b (resulting in a concomitant cooling in the cheek region), a comparison between such regions is further preferable. Likewise, a decrease in temperature in the carotid region or neck region 40a–b also appears to occur and may be used advantageously in comparison with periorbital region 34a–b.

Although exemplary methods 70a and 70b have been provided as illustrative embodiments to classify the individual 30 as having an anxiety or a non-anxiety state, one skilled in the art will readily recognize that other classification methods using thermal image data from the human face 32 may be used according to the present invention.

The present invention as described above uses thermal image data and pattern recognition to automate the detection of anxiety in individuals. Such anxiety detection may be used in any number of applications including security applications as previously described herein. However, such applications may also include various other controllable situations. For example, the anxiety detection system and method described herein may notify your computer that you are under stress and the computer may try to soothe your tension by performing an activity, e.g., playing relaxing music, indicating to the user that exercises may be needed, etc. In such a system, for example, the thermal camera is used as part of a user interface to the overall system.

Further, for example, other applications that require monitoring of physiological states non-invasively, e.g., such as from a distance, may also be performed. For example, currently, some physiological states are typically monitored in a setting using invasive transducing technology, psychiatric evaluations, polygraph evaluations, etc. The present invention may be used in a non-invasive manner in such applications, e.g., psychiatric evaluation, polygraph testing, or any other advantageous application where invasiveness is considered a liability.

The present invention is able to perform many of the advantages described herein due to one or more of the following: that thermal facial images can be acquired and analyzed, that certain thermal patterns or signatures are generally reproduced in individuals across a large population, that specific regional thermal changes in the face correspond directly to altered physiological states (e.g., anxiety states), and/or that induced anxiety is particularly associated with a specific thermal facial signature (e.g., increased temperatures in the periorbital region).

All references cited herein are incorporated in their entirety as if each were incorporated separately. This invention has been described with reference to illustrative embodiments and is not meant to be construed in a limiting sense. Various modifications of the illustrative embodiments, as well as additional embodiments of the invention, will be apparent to persons skilled in the art upon reference to this description.

What is claimed is:

1. A method to detect a physiological state of a person, the method comprising:
    providing thermal image data of at least a region of a face of a person, wherein providing the thermal image data comprises providing thermal image data of at least a periorbital region of an eye of the person representative of blood flow to at least eye musculature in the periorbital region; and
    using the thermal image data to determine a physiological state of the person.

2. The method of claim 1, wherein using the thermal image data comprises using the thermal image data to determine anxiety in the person.

3. The method of claim 2, wherein using the thermal image data comprises detecting a change, over a plurality of frames, in the thermal image data when the person is experiencing anxiety.

4. The method of claim 1, wherein providing the thermal image data comprises providing thermal image data of at least the periorbital region of the eye of the person and of another region of the face, and further wherein using the thermal image data to determine the physiological state of the person comprises comparing the thermal image data of the periorbital region of the eye of the person to thermal data of the other region of the face.

5. The method of claim 4, wherein the other region of the face comprises a cheek region of the face.

6. The method of claim 1, wherein using the thermal image data comprises comparing the thermal image data to a baseline reference.

7. The method of claim 1, wherein providing the thermal image data comprises providing mid-infrared thermal image data of the at least one region of the face and far-infrared thermal image data of the least one region of the face.

8. The method of claim 1, wherein providing thermal image data of at least a region of a face of a person comprises:
providing thermal image data of a scene; and
selecting thermal image data of the face of the person from the thermal image of the scene.

9. The method of claim 1, wherein providing thermal image data of at least a region of a face of a person comprises:
providing thermal image data of a face of the person; and
identifying thermal image data for one or more regions of the face based on at least bilateral symmetry of the thermal image data of the face.

10. A detection system to detect a physiological state of a person, the system comprising:
a thermal infrared image device operable to provide thermal image data of at least a region of a face of a person, wherein the region of the face comprises at least a periorbital region of an eye of the person representative of blood flow to at least eye musculature in the periorbital region; and
circuitry operable upon the thermal image data to determine a physiological state of the person.

11. The system of claim 10, where in the Circuitry is operable upon the thermal image data to determine the presence of anxiety in the person.

12. The system of claim 11, wherein the circuitry is operable to detect a change, over a plurality of frames, in the thermal image data when the person is experiencing anxiety.

13. The system of claim 10, wherein the thermal infrared image device is operable to provide thermal image data of at least the periorbital region of the eye of the person and of another region of the face, and further wherein the circuitry is operable to compare the thermal image data of the periorbital region of the eye of the person to the thermal image data of the other region of the face.

14. The system of claim 13, wherein the other region of the face comprises a cheek region of the face.

15. The system of claim 10, wherein the circuitry is operable to compare the thermal image data to a baseline reference.

16. The system of claim 10, wherein the thermal infrared image device is operable to provide mid-infrared thermal image data of the at least one region of the face and far-infrared thermal image data of the least one region of the face.

17. The system of claim 10, wherein the thermal infrared image device is operable to provide thermal image data of a scene and to select thermal image data of the face of the person from the thermal image of the scene.

18. The system of claim 10, wherein the thermal infrared image device is operable to provide thermal image data of a face of the person and to identify thermal image data for one or more regions of the face based on at least bilateral symmetry of the thermal image data of the face.

* * * * *

UNITED STATES PATENT AND TRADEMARK OFFICE
CERTIFICATE OF CORRECTION

PATENT NO.       : 6,996,256 B2                                      Page 1 of 1
APPLICATION NO.  : 09/776470
DATED            : February 7, 2006
INVENTOR(S)      : Ioannis Pavlidis It is certified that error appears in the above-identified patent and that said Letters Patent is hereby corrected as shown below:

On the title page item [75], insert inventor James A. Levine

Signed and Sealed this

Nineteenth Day of August, 2008

JON W. DUDAS
*Director of the United States Patent and Trademark Office*